United States Patent [19]

Schellpfeffer

[11] Patent Number: 5,626,606
[45] Date of Patent: May 6, 1997

[54] LAPAROSCOPIC TISSUE RETRIEVAL FORCEPS

[76] Inventor: Michael A. Schellpfeffer, 1400 75th St., Kenosha, Wis. 53143

[21] Appl. No.: 500,699

[22] Filed: Jul. 11, 1995

[51] Int. Cl.⁶ ............................................. A61B 17/28
[52] U.S. Cl. ................................. 606/205; 606/158
[58] Field of Search .......................... 606/205, 206, 606/207, 119, 122, 158, 208; 128/323, 324

[56] References Cited

U.S. PATENT DOCUMENTS

| | | | |
|---|---|---|---|
| 1,672,570 | 6/1928 | Breck | 606/122 |
| 2,637,320 | 5/1953 | Greenberg | 606/122 |
| 3,789,849 | 2/1974 | Laufe et al. | 606/122 |
| 4,300,564 | 11/1981 | Furihata | 606/207 |
| 4,997,435 | 3/1991 | Demeter | 606/127 |
| 5,019,092 | 5/1991 | Klintmain | 606/207 |
| 5,176,687 | 1/1993 | Hasson et al. | 606/114 |
| 5,190,561 | 3/1993 | Graber | 606/127 |
| 5,192,284 | 3/1993 | Pleatman | 606/114 |
| 5,217,468 | 6/1993 | Clements | 606/127 |
| 5,275,609 | 1/1994 | Pingleton et al. | 606/170 |
| 5,330,483 | 7/1994 | Heaven et al. | 606/114 |
| 5,370,647 | 12/1994 | Graber et al. | 606/127 |

*Primary Examiner*—Michael Powell Buiz
*Assistant Examiner*—Kevin Truong
*Attorney, Agent, or Firm*—Medlen & Carroll, LLP

[57] ABSTRACT

This laparoscopic tissue retrieval forceps is a non-disposable medical device designed to facilitate the removal of surgical tissue specimens from various body cavities through small incisions. It consists of two separate mirror image members. Each member then consists of a blade portion 10, a shank portion 12, a locking mechanism 14, and a handle portion 16. Blade portion 10 and shank portion 12 are of various sizes to accommodate various sizes of incisions and various body cavities. Blade portion 10 of each member is introduced into a body cavity through a small surgical incision along opposing sides of the surgical tissue specimen or retrieval bag/sac. The two members of the device are joined together at locking mechanism 14. Traction is applied to handle portion 16 of the device to facilitate tissue retrieval.

16 Claims, 4 Drawing Sheets

FIG 1A
FIG 1B
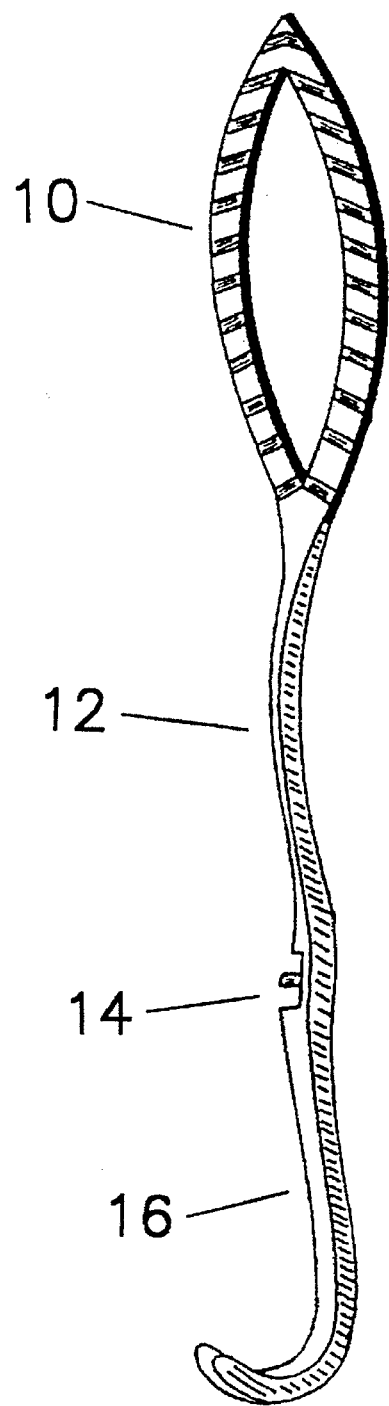
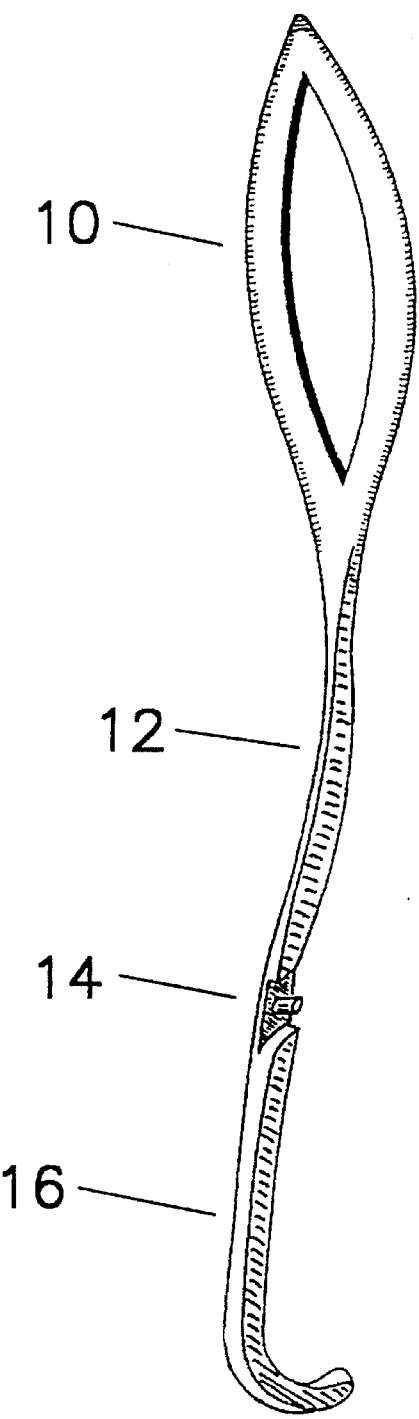

LAPAROSCOPIC TISSUE RETRIEVAL FORCEPS

BACKGROUND—FIELD OF INVENTION

This medical device facilitates the removal of surgical tissue specimens from various body cavities through small surgical incisions.

BACKGROUND—PRIOR ART

With the rapid advances in operative laparoscopy/minimally invasive surgery many conventional surgical techniques are being critically assessed and modified. By definition, laparoscopic/minimally invasive surgeries are performed using very small surgical incisions. This type of surgery is not limited to the abdominal cavity. Various body cavities are routinely accessed via small telescope and trocar systems through small surgical incisions. To date, one aspect of these types of surgeries is not well developed. This is the task of actually removing a surgical tissue specimen from a body cavity through a small surgical incision.

Several medical devices are available to reduce the size of a surgical tissue specimen prior to removal from a body cavity. This type of device works on the principle of mechanically fragmenting the resected tissue for easier removal through a small surgical incision. An example of this type of device is U.S. Pat. No. 5,275,609 (1994) to Pingleton and Thomson. The problems with this type of device are:

(a) it reduces the chances for accurate pathologic diagnosis by the fragmentation process.
(b) it increases the possibility of spreading infection in instances where infected tissue is removed.
(c) it increases the potential for spreading malignant disease in instances where cancerous tissue is removed.

Multiple plastic retrieval bags/sacs are also available that allow the removal of an intact surgical tissue specimen from a body cavity. Two examples of this type of device are U.S. Pat. No. 5,337,754 (1993) to Heaven et al and U.S. Pat. No. 5,192,284 (1992) to Pleatman. The difficulty with these retrieval bags/sacs is that they do not always allow easy removal of surgical tissue specimens through small surgical incisions. This is due to the physical characteristics of the flexible plastic bag/sac. As the bag/sac is removed from a body cavity, the surgical tissue specimen is forced into the bottom of the bag/sac as it is drawn through the small surgical incision. This distends the bag/sac and creates an even larger diameter that must traverse the small diameter of the surgical incision. In many cases, the most difficult part of the operation becomes the removal of the surgical tissue specimen in this manner.

More recently, several retrieval bags/sacs are available with support structures incorporated into the bag/sac lining. Examples of this type of device are U.S. Pat. No. 5,370,647 (1993) to Graber et al, U.S. Pat. No. 5,330,183 (1992) to Heaven and Schuler, U.S. Pat. No. 5,217,468 (1991) to Clement, U.S. Pat. No. 5,190,561 (1991) to Graber, U.S. Pat. No. 5,176,687 (1991) to Hasson, and U.S. Pat. No. 4,997,435 (1989) to Demeter. This type of device reduces the size of a surgical tissue specimen to its smallest diameter. It does not, however, provide a rigid external support around the surgical tissue specimen or retrieval bag/sac. It also does not allow independent traction to be applied along the axis of the surgical tissue specimen or retrieval bag/sac to allow for easy removal from a body cavity.

For several centuries obstetrical forceps have been used to facilitate passage of a baby's head through the maternal birth canal. Obstetrical forceps provide a rigid external support to a baby's head during the assisted passage through the birth canal. Obstetrical forceps also allow an obstetrician to apply a variable amount of independent traction along the axis of the device to expedite delivery of a baby.

OBJECTS AND ADVANTAGES

With the above mentioned obstetric concepts in mind and recognizing the limitations of the existing technology, the laparoscopic tissue retrieval forceps is presented. Accordingly, several objects and advantages of the laparoscopic tissue retrieval forceps are:

(a) to facilitate the removal of a surgical tissue specimen from a body cavity through a small surgical incision.
(b) to allow the removal from a body cavity of an intact surgical tissue specimen through a small surgical incision.
(c) to provide a rigid external support structure around a surgical tissue specimen or retrieval bag/sac during removal from a body cavity.
(d) to allow independent traction to be applied to a surgical tissue specimen or retrieval bag/sac to facilitate passage out of a body cavity.

Further objects and advantages of the device will become apparent from consideration of the drawings and ensuing description.

SUMMARY

This is a non-disposable medical device used to facilitate the retrieval from a body cavity of a surgical tissue specimen through a small surgical incision.

DESCRIPTION OF DRAWINGS

FIG. 1a and 1b show the right member of the laparoscopic tissue retrieval forceps with an inside and outside view respectively.

Figure 2A:
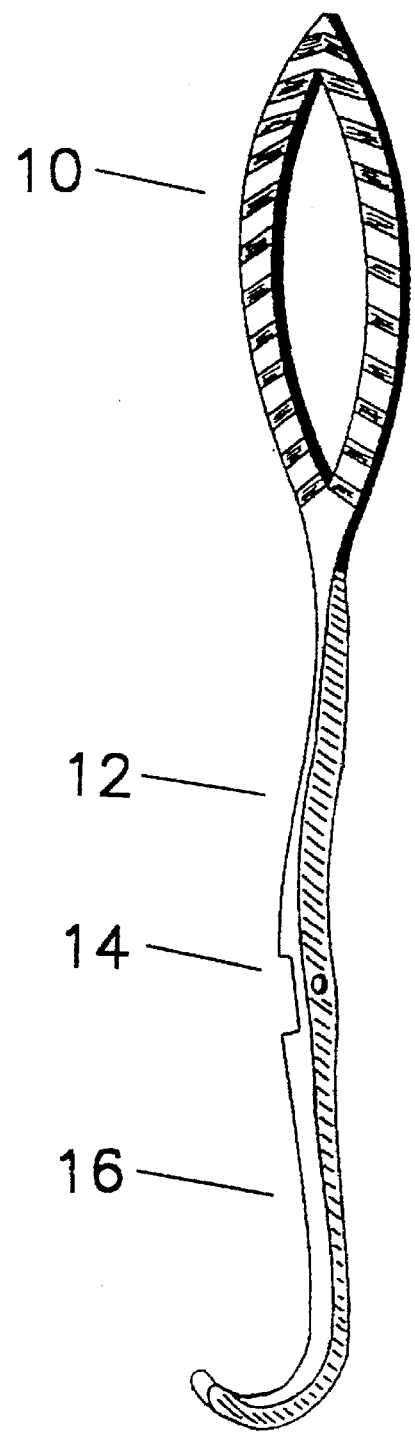
FIG. 2a and 2b show the left member of the laparoscopic tissue retrieval forceps with an inside and outside view respectively.
Figure 2B:
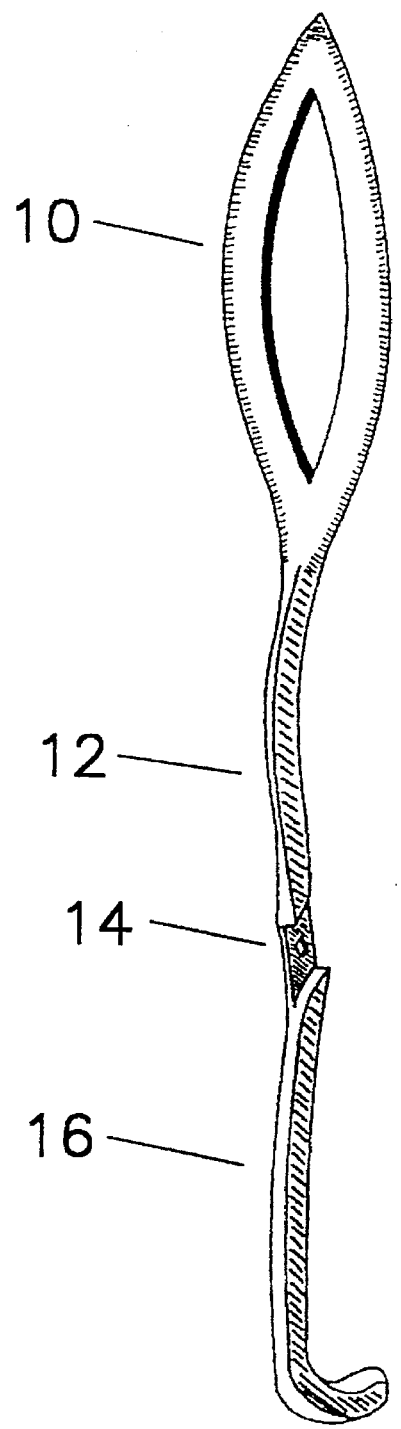

REFERENCE NUMERALS IN DRAWINGS 10 blade portion  22 laparoscopic tissue retrieval
12 shank portion  forceps
14 locking mechanism  24 abdominal cavity
16 handle portion  26 abdominal wall
18 laparoscope
20 tissue retrieval sac

DESCRIPTION

Figure 3:
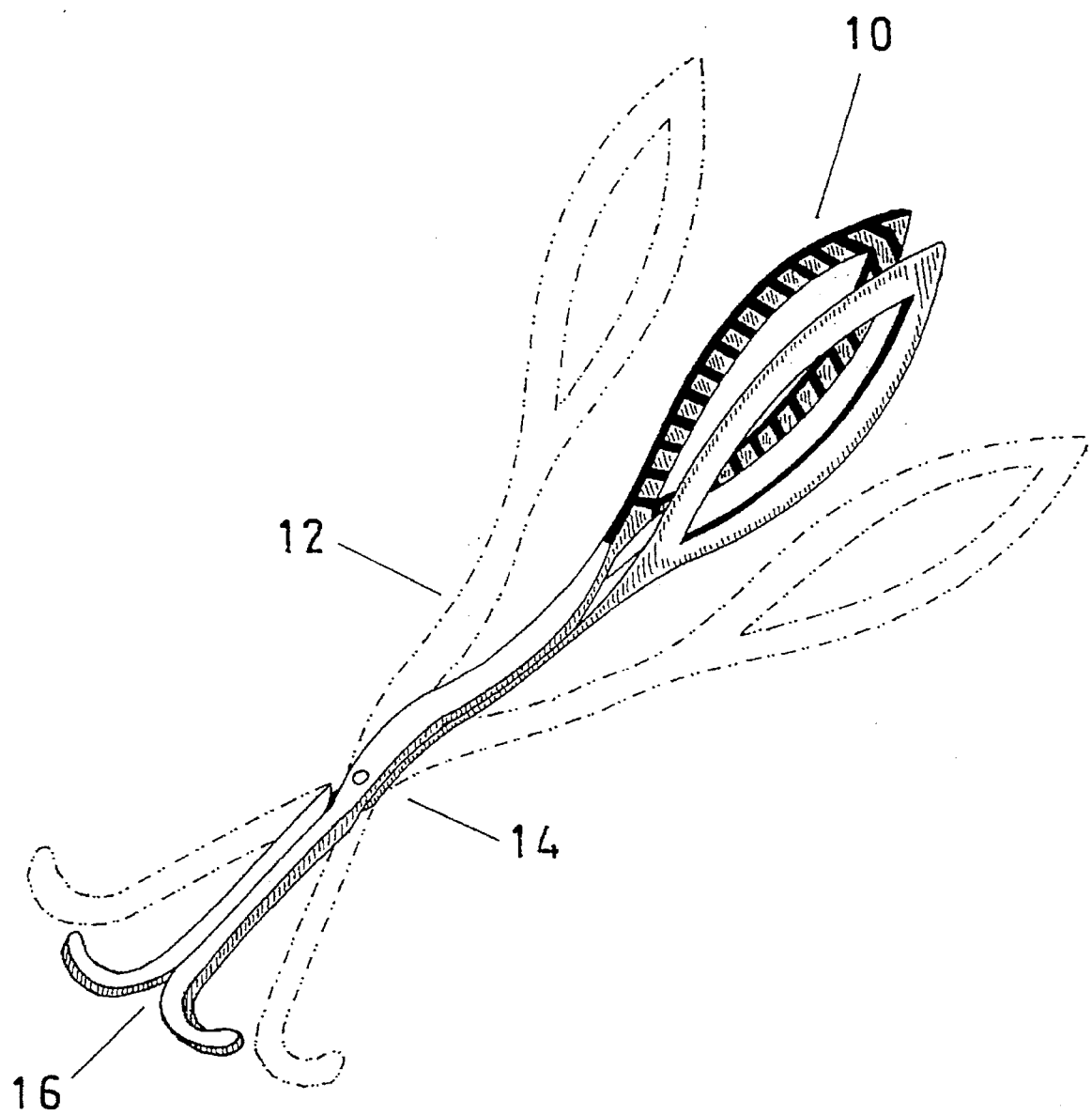
FIG. 3 shows the laparoscopic tissue retrieval forceps joined together for use in the closed and open position.

A laparoscopic tissue retrieval forceps is a medical device designed to facilitate removal of surgical tissue specimens from various body cavities through small surgical incisions. A typical embodiment of this device is illustrated in FIG. 3. It is a non-disposable device designed and manufactured for repeated use and sterilization. It is made of surgical quality martensitic precipitation/age-hardening stainless steel. Using an EDM (electro-discharge machine) wire cutting tool the device is rough cut to form. Further processing of the device is done with milling machines. The device is then heat treated to harden the metal to complete strength and polished to its final form. The anticipated means of manufacture of this device is either investment casting, forging, or mass production EDM wire cutting machining.

The device consists of two separate members that lock together in apposition side to side in a scissors-like fashion when in use. This is illustrated in FIG. 3. Each member is a mirror image of the other. It consists of a blade.. portion 10, a shank portion 12, a locking mechanism 14, and a handle portion 16. Blade portion 10 is at one end of the device connected by shank portion 12 to locking mechanism 14, which in turn is connected to handle portion 16. This is illustrated in FIG. 1a and b, and FIG. 2a and b.

Blade portion 10 of the device is curved toward its axis in its length and width. It is torpedo-shaped and its edges are beveled on the outside diameters. The body of blade portion 10 is fenestrated. The inside aspect of blade.. portion 10 is a herringbone notched surface pointing toward the front end of the device. Blade portion 10 is of various widths.

Shank portion 12 of the device is curved as it courses from blade portion 10 to locking mechanism 14. Consequently, blade portion 10 and handle portion 16 are parallel. Shank portion 12 overlaps top to bottom when locked together in use. Shank portion 12 is of various lengths.

Locking mechanism 14 of the device is a detachable pin in hole right-handed scissoring action. Its location divides shank portion 12 and handle portion 16.

Handle portion 16 of the device is created when the device is locked together in apposition side to side. The end of handle portion 16 is blunt. It is curved 180 degrees out from the midline of the device toward blade portion 10.

OPERATION OF INVENTION

The laparoscopic tissue retrieval forceps is cleaned and sterilized using standard surgical sterilization procedures for stainless steel non-disposable surgical instruments. This medical device is used in accordance with standard sterile surgical technique.

During many laparoscopic/minimally invasive surgical procedures a surgical tissue specimen will need to be removed. The surgical tissue specimen is isolated either alone or in a retrieval bag/sac. In the case of an isolated surgical tissue specimen, the specimen is grasped with a laparoscopic grasping instrument and brought up to the inner body cavity surface. In the case of a laparocopic retrieval bag/sac, the bag/sac with an enclosed surgical tissue specimen is drawn up to the inner body cavity surface. If the surgical tissue specimen or retrieval bag/sac is not easily withdrawn through the intended surgical incision site the laparoscopic tissue retrieval forceps is used.

Figure 4:
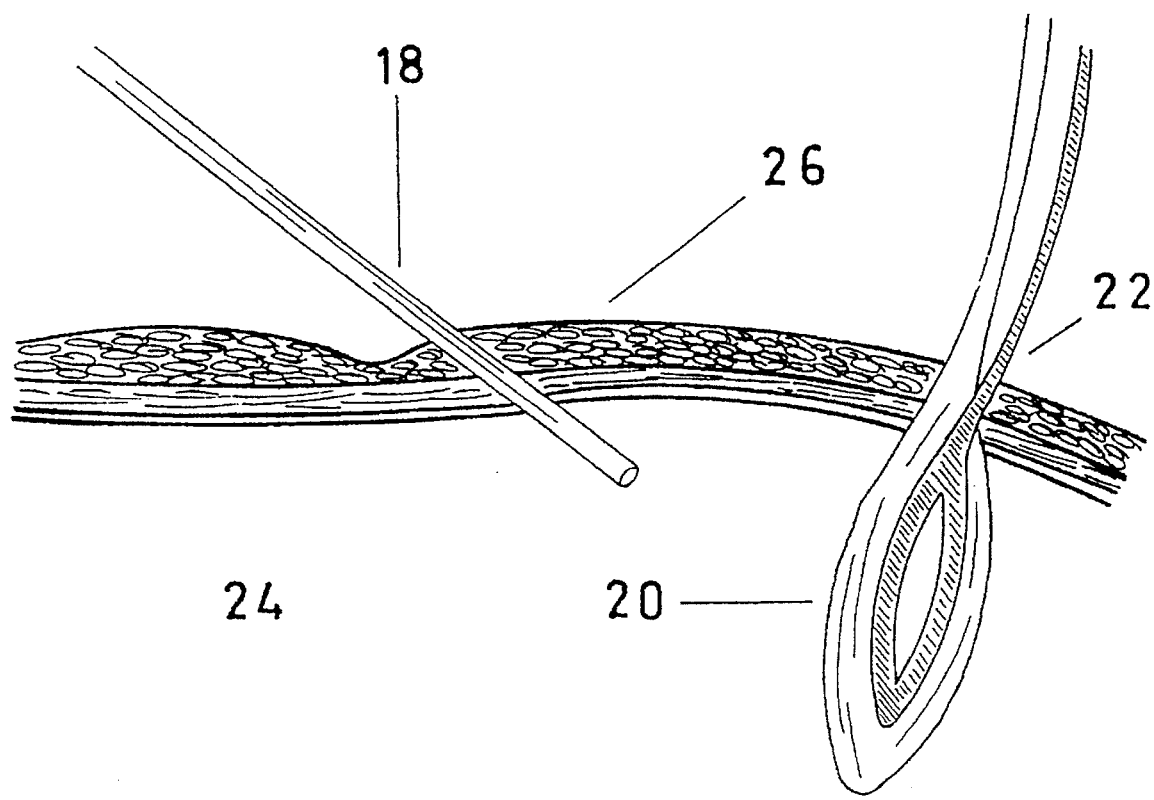
FIG. 4 shows the laparocopic tissue retrieval forceps applied to a surgical tissue specimen through a small surgical incision.

The laparoscopic tissue retrieval forceps is introduced into the body cavity through the surgical incision intended for removal of the surgical tissue specimen. Each member of the device is introduced separately along opposing: sides of the surgical tissue specimen or retrieval bag/sac. Consecutively, this is accomplished by placing the inside aspect of blade portion 10 of each member parallel to and along side of the surgical tissue specimen or retrieval bag/sac at the outer body surface. Blade portion 10 is then gently introduced into the body cavity between the surgical tissue specimen or retrieval bag/sac and the incision edge. This is illustrated in FIG. 4.

The device is joined together at locking mechanism 14 in a scissors-like fashion illustrated in FIG. 3. The curve in shank portion 12 allows the surgical tissue specimen or retrieval bag/sac to be positioned so that it does Rot interfere with locking the device or applying traction to the device. Traction is applied to handle portion 16 of the device perpendicular to the outer body surface. The surgical tissue specimen or retrieval bag/sac is drawn through the surgical incision with blade portion 10 of the device providing rigid external support to the tissue specimen or retrieval bag/sac. This action distends the surgical incision to its maximum diameter while minimizing the diameter of the material being removed. At this point, if the surgical tissue specimen or retrieval bag/sac cannot be removed from the body cavity then and only then would the surgical incision need to be enlarged. Once the specimen is removed from the body cavity the surgical site is routinely inspected to assess the necessity and/or degree of repair necessary to adequately close the surgical wound site.

CONCLUSIONS, RAMIFICATIONS AND SCOPE

Accordingly, the reader will see that the laparoscopic tissue retrieval forceps facilitates the removal of a surgical tissue specimen that would otherwise require fragmentation of the surgical tissue specimen or enlargement of the surgical incision. The unique advantages that the laparoscopic tissue retrieval forceps provide over currently patented devices are:

(a) a rigid external support to minimize the diameter of the surgical tissue specimen to be removed.

(b) protection of the integrity of the surgical tissue specimen.

(c) the ability to apply independent external traction along the axis of the surgical tissue specimen to facilitate its passage out of a body cavity.

The device has the potential for numerous modifications to tailor the instrument to an intended task. Blade portion 10 can be of various sizes to accommodate various incision sizes and body cavities. It can also be non-fenestrated. The inside aspect of blade portion 10 can have different types of serrations or grooves to better facilitate a particular task. Shank portion 12 can be various lengths to allow easier access to certain body cavities. It can also be straight or curved in various fashions depending upon the task to be performed. Locking mechanism 14 can be either right or left-handed. Similar to obstetrical forceps, locking mechanism 14 has the potential for other types of detachable and non-detachable systems. Finally, handle portion 16 can be larger or smaller depending upon the task. It can also be made with an additional locking mechanism to better secure a surgical tissue specimen for removal.

Modified versions of this device could potentially be used to facilitate removal of tissue from the thoracic cavity during thoracoscopy as well as the pelvic cul-de-sac via a culdotomy incision. A modified version of this device has the potential for facilitating the removal of foreign bodies from various body orifices including the vagina, lower rectum, and oral cavity. A much smaller version of the device could be used to facilitate the removal of surgical tissue specimens from larger joint cavities during arthroscopy as well as sinus and nasal cavities during endoscopic sinus surgery.

Thus, the scope of the invention should be determined by the appended claims and their legal equivalents, rather than by the examples given.

I claim:

1. A method of removing tissue, comprising:
 a) providing
  i) a patient having tissue to be removed, and ii) a tissue removal device, comprising first and second detachable members, said members each comprising a blade portion, a shank portion and a connection means;

b) making a surgical incision in said patient, said surgical incision dimensioned to permit the introduction of said device;

c) introducing said first member of said device into said surgical incision under conditions such that said first member contacts said tissue;

d) introducing said second member of said device into said surgical incision under conditions such that said second member contacts said tissue;

e) connecting said first and second members via said connection means under such conditions that said tissue is encompassed by said blade portions of said first and second members; and f) removing said tissue from said patient through said surgical incision.

2. The method of claim 1, wherein said connection means of said first member comprises a pin and said connection means of said second member comprises a hole dimensioned to fit said pin.

3. The method of claim 1, wherein said tissue is suspected to be cancerous.

4. The method of claim 1, wherein said tissue is located in said patient's thoracic cavity.

5. The method of claim 1, wherein said tissue is located in said patient's peritoneal cavity.

6. The method of claim 1, wherein said tissue is located in said patient's abdominal cavity.

7. The method of claim 1, wherein said tissue is located in said patient's pelvic cavity.

8. The method of claim 1, wherein said tissue is located in said patient's joint cavity.

9. A method of removing tissue, comprising:

a) providing
   i) a patient having tissue to be removed,
   ii) a surgical tissue collection means, and iii) a tissue removal device, comprising first and second detachable members, said members each comprising a blade portion, a shank portion and a connection means;

b) making a surgical incision in :said patient, said surgical incision dimensioned to permit the introduction of said device;

c) introducing said collection means into said surgical incision such that said tissue is encompassed by said collection means;

d) introducing said first member of said device into said surgical incision under conditions, such that said first member contacts said collection means;

e) introducing said second member of said device into said surgical incision under conditions such that said second member contacts said collection means;

f) connecting said first and second members via said connection means under such conditions that said collection means is encompassed by said blade portions of said first and second members; and g) removing said collection means containing said tissue from said patient through said surgical incision.

10. The method of claim 9, wherein said connection means of said first member comprises a pin and said connection means of said second member comprises a hole dimensioned to fit said pin.

11. The method of claim 9, wherein said tissue is suspected to be cancerous.

12. The method of claim 9, wherein said tissue is located in said patient's thoracic cavity.

13. The method of claim 9, wherein said collections means comprises a bag.

14. The method of claim 9, wherein said tissue is located in said patient's abdominal cavity.

15. The method of claim 9, wherein said tissue is located in said patient's pelvic cavity.

16. The method of claim 9, wherein said tissue is located in said patient's joint cavity.

* * * * *